US008563651B2

(12) United States Patent
Kozlowski

(10) Patent No.: US 8,563,651 B2
(45) Date of Patent: *Oct. 22, 2013

(54) METHOD INVOLVING 1-BENZOTRIAZOLYL CARBONATE ESTERS OF POLY(ETHYLENE GLYCOL)

(71) Applicant: Nektar Therapeutics, San Francisco, CA (US)

(72) Inventor: Antoni Kozlowski, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/664,021

(22) Filed: Oct. 30, 2012

(65) Prior Publication Data

US 2013/0053514 A1    Feb. 28, 2013

Related U.S. Application Data

(60) Continuation of application No. 13/154,917, filed on Jun. 7, 2011, now Pat. No. 8,299,173, which is a continuation of application No. 12/756,905, filed on Apr. 8, 2010, now Pat. No. 7,977,427, which is a continuation of application No. 12/433,874, filed on Apr. 30, 2009, now Pat. No. 7,723,432, which is a continuation of application No. 12/150,136, filed on Apr. 25, 2008, now Pat. No. 7,544,738, which is a continuation of application No. 11/492,133, filed on Jul. 24, 2006, now Pat. No. 7,378,469, which is a continuation of application No. 10/727,337, filed on Dec. 2, 2003, now Pat. No. 7,101,932, which is a continuation of application No. 10/068,371, filed on Feb. 6, 2002, now Pat. No. 6,710,125, which is a division of application No. 09/740,556, filed on Dec. 18, 2000, now Pat. No. 6,376,604.

(60) Provisional application No. 60/171,834, filed on Dec. 22, 1999.

(51) Int. Cl.
| C08F 16/06 | (2006.01) |
| C08F 116/06 | (2006.01) |
| C07D 249/08 | (2006.01) |
| C07D 401/00 | (2006.01) |

(52) U.S. Cl.
USPC ............ 525/54.2; 525/56; 525/60; 525/365; 525/377; 525/403; 525/406; 528/195

(58) Field of Classification Search
USPC ............ 525/54.2, 56, 60, 365, 377, 403, 406; 528/195
See application file for complete search history.

(56) References Cited

U.S. PATENT DOCUMENTS

| 5,281,698 A | 1/1994 | Nitecki |
| 5,629,384 A | 5/1997 | Veronese et al. |
| 5,650,234 A | 7/1997 | Dolence et al. |
| 5,932,462 A | 8/1999 | Harris et al. |
| 5,985,263 A | 11/1999 | Lee et al. |
| 6,348,558 B1 | 2/2002 | Harris et al. |
| 6,376,604 B2 | 4/2002 | Kozlowski |
| 6,436,386 B1 | 8/2002 | Roberts et al. |
| 6,624,246 B2 | 9/2003 | Kozlowski |
| 6,710,125 B2 | 3/2004 | Kozlowski |
| 7,101,932 B2 | 9/2006 | Kozlowski |
| 7,378,469 B2 | 5/2008 | Kozlowski |
| 7,544,738 B2 | 6/2009 | Kozlowski |
| 7,723,432 B2 | 5/2010 | Kozlowski |
| 7,977,427 B2 | 7/2011 | Kozlowski |
| 8,299,173 B2 | 10/2012 | Kozlowski |
| 2009/0215910 A1 | 8/2009 | Kozlowski |

FOREIGN PATENT DOCUMENTS

DE            287951            3/1991

OTHER PUBLICATIONS

Fluka Catalog Cover Sheet and p. 490, (1995/96).
Greenwald, et al., "Highly Water Soluble Taxol Derivatives: 7-Polyethylene Glycol Carbamates and Carbonates," J. Org. Chem., vol. 60, pp. 331-336, (1995).
Miron, et al., "A Simplified Method for the Preparation of Succinimidyl Carbonate Polyethylene Glycol for Coupling to Proteins," Bioconj. Chem., vol. 4, pp. 568-569, (1993).
Monfardini, et al., "A Branched Monomethoxypoly(ethylene glycol) for protein modification," Bioconj. Chem. J. of Amer. Chem. Soc., vol. 6, No. 1, pp. 62-69, (1995).
Zalipsky, "Functionalized Poly(ethylene glycol) for Preparation of Biologically Relevant Conjugates," Bioconj. Chem., vol. 6, pp. 150-165, (1995).
PCT International Search Report corresponding to PCT Application No. PCT/US2000/34590 mailed on Dec. 19, 2001.
PCT Written Opinion corresponding to PCT Application No. PCT/US2000/34590 mailed on May 21, 2002.
PCT International Preliminary Examination Report corresponding to PCT Application No. PCT/US2000/34590 mailed on Jul. 16, 2002.
Shearwater Polymers, Inc., Polyethylene Glycol and Derivatives, 55 pages, (Catalog—Jul. 1997).

(Continued)

*Primary Examiner* — Nathan M Nutter
(74) *Attorney, Agent, or Firm* — Mark A. Wilson

(57) ABSTRACT

The invention provides a method comprising the steps of providing a poly(ethylene glycol) having one terminal hydroxyl group; reacting the terminal hydroxyl group of the poly(ethylene glycol) with di(1-benzotriazolyl)carbonate to form a 1-benzotriazolylcarbonate ester of the poly(ethylene glycol); reacting the 1-benzotriazolylcarbonate ester of the poly(ethylene glycol) with an amino acid to form an amino acid derivative; and reacting the amino acid derivative with a biologically active agent under conditions to form a polymer-active agent conjugate.

4 Claims, No Drawings

(56) References Cited

OTHER PUBLICATIONS

Shearwater Polymers, Inc., Polyethylene Glycol and Derivatives: Functionalized Biocompatible Polymers for Research and Pharmaceuticals, pp. 1-50, (Catalog—Jan. 2000).

European Opposition Brief Against EP 1 259 563 B1 (English Translation).

Shearwater Polymers, Inc., Polyethylene Glycol and Derivatives, 50 pages, (Catalog—Mar. 1995).

European Preliminary Opinion from Opposition Board of the EPO dated Jul. 13, 2011.

First Official Communication corresponding to European Application No. 00 986 602.1-1214 dated Mar. 11, 2004.

Further Communication corresponding to European Application No. 00 986 602.1-062 dated Aug. 2, 2006.

METHOD INVOLVING 1-BENZOTRIAZOLYL CARBONATE ESTERS OF POLY(ETHYLENE GLYCOL)

CROSS-REFERENCE TO RELATED APPLICATIONS

This application is a continuation of U.S. application Ser. No. 13/154,917, filed Jun. 7, 2011, now U.S. Pat. No. 8,299,173, which is a continuation of U.S. application Ser. No. 12/756,905, filed Apr. 8, 2010, now U.S. Pat. No. 7,977,427, which is a continuation of U.S. application Ser. No. 12/433,874, filed Apr. 30, 2009, now U.S. Pat. No. 7,723,432, which is a continuation of U.S. application Ser. No. 12/150,136, filed Apr. 25, 2008, now U.S. Pat. No. 7,544,738, which is a continuation of U.S. application Ser. No. 11/492,133, filed Jul. 24, 2006, now U.S. Pat. No. 7,378,469, which is a continuation of U.S. application Ser. No. 10/727,337, filed Dec. 2, 2003, now U.S. Pat. No. 7,101,932, which is a continuation of U.S. application Ser. No. 10/068,371, filed Feb. 6, 2002, now U.S. Pat. No. 6,710,125, which is a divisional of U.S. application Ser. No. 09/740,556, filed Dec. 18, 2000, now U.S. Pat. No. 6,376,604, and claims the benefit of priority of U.S. Provisional Application No. 60/171,834, filed Dec. 22, 1999, each of which is incorporated herein by reference in its entirety.

FIELD OF THE INVENTION

This invention relates to activated poly(ethylene glycol) derivatives and methods of preparing such derivatives.

BACKGROUND OF THE INVENTION

Covalent attachment of the hydrophilic polymer, poly(ethylene glycol), abbreviated PEG, also known as poly(ethylene oxide), abbreviated PEO, to molecules and surfaces is of considerable utility in biotechnology and medicine. In its most common form, PEG is a linear polymer terminated at each end with hydroxyl groups:

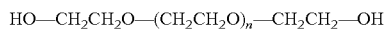

The above polymer, alpha-,omega-dihydroxylpoly(ethylene glycol), can be represented in brief form as "HO-PEG-OH" where it is understood that the "PEG" symbol represents the following structural unit:

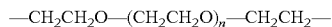

where n typically ranges from about 3 to about 4000.

PEG is commonly used as methoxy-PEG-OH, or mPEG in brief, in which one terminus is the relatively inert methoxy group, while the other terminus is a hydroxyl group that is subject to ready chemical modification. The structure of mPEG is given below.

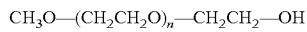

mPEG

Random or block copolymers of ethylene oxide and propylene oxide, shown below, are closely related to PEG in their chemistry, and they can be substituted for PEG in many of its applications:

wherein each R is independently H or $CH_3$.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J. Org. Chem.*, 60:331-336 (1995).

To couple PEG to a molecule, such as a protein, it is often necessary to "activate" the PEG by preparing a derivative of the PEG having a functional group at a terminus thereof. The functional group can react with certain moieties on the protein, such as an amino group, thus forming a PEG-protein conjugate.

In U.S. Pat. No. 5,650,234, which is incorporated by reference herein in its entirety, a 1-benzotriazolylcarbonate ester of poly(ethylene glycol) is described. The multi-step process described in the '234 patent for forming the 1-benzotriazolylcarbonate ester of PEG includes reaction of a PEG molecule with the volatile and hazardous compound, phosgene, in order to form a PEG chloroformate intermediate. The use of phosgene in the process results in the formation of HCl, which can cause degradation of the PEG backbone. Due to the volatile nature of phosgene, and the resulting safety and quality problems associated with its use, there is a need in the art for a method for preparing 1-benzotriazolylcarbonate esters of PEG without using phosgene.

SUMMARY OF THE INVENTION

The invention provides a method for the preparation of a 1-benzotriazolylcarbonate ester of a water-soluble and non-peptidic polymer by reacting the polymer with di(1-benzotriazolyl)carbonate ("di-BTC"). Using the invention, the 1-benzotriazolylcarbonate ester can be formed in a single step and without using phosgene, thereby avoiding the safety and quality problems associated with that compound.

The method of the invention includes providing a water-soluble and non-peptidic polymer having at least one terminal hydroxyl group and reacting the terminal hydroxyl group of the water-soluble and non-peptidic polymer with di(1-benzotriazolyl)carbonate to form the 1-benzotriazolylcarbonate ester of the water-soluble and non-peptidic polymer. Examples of suitable water-soluble and non-peptidic polymers include poly(alkylene glycol), poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof. In one embodiment, the polymer is poly(ethylene glycol) having an average molecular weight from about 200 Da to about 100,000 Da.

The reaction step can be conducted in the presence of an organic solvent and a base. Examples of suitable organic solvents include methylene chloride, chloroform, acetonitrile, tetrahydrofuran, dimethylformamide, dimethyl sulfoxide, and mixtures thereof. The base can be, for example, pyridine, dimethylaminopyridine, quinoline, trialkylamines, and mixtures thereof.

The method of the invention can further include reacting the 1-benzotriazolylcarbonate ester of the water-soluble and non-peptidic polymer with the amino groups of a second polymer having a plurality of primary amino groups, such as a protein, poly(ethylene glycol), aminocarbohydrates, or poly(vinylamine), to form a cross-linked polymer. Additionally, the 1-benzotriazolylcarbonate ester can be reacted with either an amino acid, such as lysine, to form a polymeric amino acid derivative, or a biologically active agent to form a biologically active polymer conjugate.

DETAILED DESCRIPTION OF THE INVENTION

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate portions of molecules that perform some function or activity and are reactive with other molecules. The term "active," when used in conjunction with "functional groups", is intended to include those functional groups that react readily with electrophilic or nucleophilic groups on other molecules, in contrast to those groups that require strong catalysts or highly impractical reaction conditions in order to react. For example, as would be understood in the art, the term "active ester" would include those esters that react readily with nucleophilic groups such as amines. Typically, an active ester will react with an amine in aqueous media in a matter of minutes, whereas certain esters, such as methyl or ethyl esters, require a strong catalyst in order to react with a nucleophilic group.

The term "linkage" or "linker" is used herein to refer to groups or bonds that normally are formed as the result of a chemical reaction and typically are covalent linkages. "Hydrolytically stable linkages" means that the linkages are substantially stable in water and do not react with water at useful pHs, e.g., under physiological conditions for an extended period of time, perhaps even indefinitely. "Hydrolytically unstable" or "hydrolytically degradable" linkages means that the linkages are degradable in water or in aqueous solutions, including for example, blood. "Enzymatically unstable" or "enzmatically degradable" linkages means that the linkage can be degraded by one or more enzymes. As understood in the art, PEG and related polymers may include degradable linkages in the polymer backbone or in the linker group between the polymer backbone and one or more of the terminal functional groups of the polymer molecule.

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The invention provides a method for the preparation of a 1-benzotriazolylcarbonate ester (also referred to as a BTC ester) of a water-soluble and non-peptidic polymer, wherein a terminal hydroxyl group of a water-soluble and non-peptidic polymer is reacted with di(1-benzotriazolyl)carbonate, the structure of which is shown below, to form the 1-benzotriazolylcarbonate ester.

Di(1-benzotriazolyl)carbonate, which should not pose significant safety or handling problems as a reagent and should not cause degradation of the polymer backbone, can be purchased as a 70% (w/w) mixture with 1,1,2-trichloroethane from Fluka Chemical Corporation of Milwaukee, Wis.

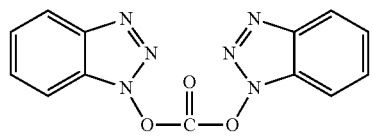

di(1-benzotriazolyl)carbonate (diBTC)

The polymer backbone of the water-soluble and non-peptidic polymer can be poly(ethylene glycol) (i.e. PEG). However, it should be understood that other related polymers are also suitable for use in the practice of this invention and that the use of the term "PEG" or "poly(ethylene glycol)" is intended to be inclusive and not exclusive in this respect. The term, "PEG", includes poly(ethylene glycol) in any of its forms, including alkoxy PEG, difunctional PEG, multi-armed PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate an immune response so that an organism can tolerate the presence of the agent. PEG conjugates tend not to produce a substantial immune response or cause clotting or other undesirable effects. PEG, having the formula —$CH_2CH_2O$—($CH_2CH_2O)_n$—$CH_2CH_2$—, where n is from about 3 to about 4000, typically from about 3 to about 2000, is one useful polymer in the practice of the invention. PEGs having a molecular weight of from about 200 Da to about 100,000 Da are particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(—PEG-OH)$_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

Those of ordinary skill in the art will recognize that the foregoing list of substantially water soluble and non-peptidic polymer backbones is by no means exhaustive and is merely illustrative, and that all polymeric materials having the qualities described above are contemplated.

For purposes of illustration, a simplified reaction scheme for the method of the invention is shown below.

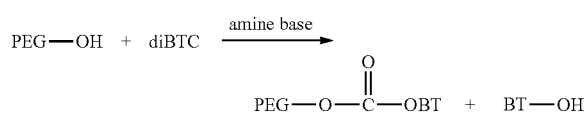

wherein BT is

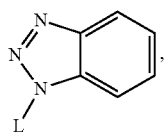

L being the point of bonding to the oxygen atom.

In one embodiment, the reaction between the polymer and diBTC takes place in an organic solvent and in the presence of a base. Examples of suitable organic solvents include methylene chloride, chloroform, acetonitrile, tetrahydrofuran, dimethylformamide, dimethyl sulfoxide, and mixtures thereof. Amine bases, such as pyridine, dimethylaminopyridine, quinoline, trialkylamines, including triethylamine, and mixtures thereof, are examples of suitable bases. In one aspect of the invention, the molar ratio of di(1-benzotriazolyl) carbonate to the water-soluble and non-peptidic polymer is about 30:1 or less.

In one embodiment, the water-soluble and non-peptidic polymer has the structure R'-POLY-OH and the 1-benzotriazolylcarbonate ester of the water-soluble and non-peptidic polymer has the structure:

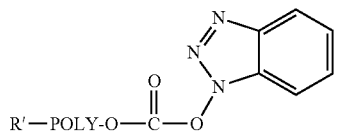

wherein POLY is a water-soluble and non-peptidic polymer backbone, such as PEG, and R' is a capping group. R' can be any suitable capping group known in the art for polymers of this type. For example, R' can be a relatively inert capping group, such as an alkoxy group (e.g. methoxy). Alternatively, R' can be a functional group. Examples of suitable functional groups include hydroxyl, protected hydroxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, protected amine, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate. The functional group is typically chosen for attachment to a functional group on a biologically active agent.

As would be understood in the art, the term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl or ethyl. Other protecting groups known in the art may also be used in the invention.

In another embodiment, the water-soluble and non-peptidic polymer has the structure HO—POLY$_a$-R(POLY$_b$-X)$_q$ and the 1-benzotriazolylcarbonate ester of the water-soluble and non-peptidic polymer has the structure

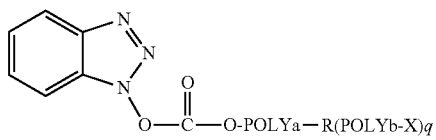

wherein POLY$_a$ and POLY$_b$ are water-soluble and non-peptidic polymer backbones, such as PEG, that may be the same or different; R is a central core molecule, such as glycerol or pentaerythritol; q is an integer from 2 to about 300; and each X is a capping group. The X capping groups may be the same as discussed above for R'.

In another aspect, a difunctional or higher functional BTC ester of the water-soluble and non-peptidic polymer is reacted with at least two amino groups of a second polymer having a plurality of primary amino groups, such as amino PEGs or other multifunctional amine polymers, such as proteins, aminocarbohydrates, or poly(vinylamine), to form cross-linked polymers. The amine polymer will generally have three or more available amino groups. Such polymers form hydrogels; that is, they become highly hydrated in aqueous media, but do not dissolve. Since these hydrogels are commonly biocompatable and may be degradable, many biomedical applications are possible in the areas of drug delivery, wound covering, and adhesion prevention.

A further embodiment of the invention involves the reaction of BTC esters of water-soluble and non-peptidic polymers with amino acids to form amino acid derivatives. In one embodiment, a PEG-BTC ester is reacted with lysine to form a polymeric lysine derivative. For example, one such lysine derivative is a doubly PEGylated lysine, wherein the two PEGs are linked to the lysine amines by carbamate bonds, as shown below.

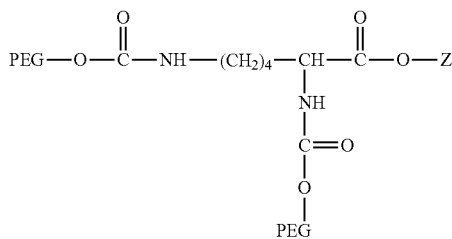

wherein PEG is poly(ethylene glycol) and Z is selected from the group consisting of H, N-succinimidyl, or 1-benzotriazolyl.

Such PEG derivatives of lysine are useful as reagents for preparation of PEG derivatives of proteins. These PEG derivatives often offer advantages over non-PEGylated proteins, such as longer circulating life-times in vivo, reduced rates of proteolysis, and lowered immunogenicity. In another aspect, PEG BTC derivatives are used directly in attaching PEG to proteins through carbamate linkages and may offer advantages similar to those described for the lysine PEG derivatives.

BTC esters of water-soluble and non-peptidic polymers can also be reacted with biologically active agents to form biologically active polymer conjugates. Examples of biologically active agents include peptides, proteins, enzymes, small molecule drugs, dyes, lipids, nucleosides, oligonucleotides, cells, viruses, liposomes, microparticles and micelles.

The invention also includes 1-benzotriazolylcarbonate esters of water-soluble and non-peptidic polymers prepared according to the above-described process. As noted above, it is believed that polymer derivatives prepared according to the invention exhibit higher quality because degradation of the polymer backbone caused by phosgene is avoided. Further, since the method of the invention requires only one step and fewer reactants, process efficiency is enhanced and cost is reduced.

The following examples are given to illustrate the invention, but should not be considered in limitation of the invention.

EXAMPLES

Example 1

Preparation of mPEG$_{5000}$BTC

A solution of mPEG$_{5000}$-OH (MW 5000, 15 g, 0.003 moles), di(1-benzotriazolyl)carbonate (4.0 g of 70% mixture, 0.000945 moles), and pyridine (2.2 ml) in acetonitrile (30 ml) was stirred at room temperature under nitrogen overnight. The solvent was removed by distillation, the residue was dissolved in 80 ml of methylene chloride, and the resulting solution was added to 850 ml of ethyl ether. The mixture was cooled to 0-5° C. and the precipitate was collected by filtration. The precipitation process was then repeated to obtain a white solid which was dried under vacuum at room temperature to yield 13.5 g of product which was shown by $^1$H NMR to be 100% substituted. $^1$H NMR (dmso d-6): 3.23 ppm, CH$_3$O; 3.51 ppm, O—CH$_2$CH$_2$—O; 4.62 ppm, m, mPEG-O—CH$_2$—OCO$_2$—; 7.41-8.21, complex mult., benzotriazole protons.

Example 2

Preparation of mPEG$_{20,000}$BTC

A solution of mPEG$_{20,000}$-OH (MW 20,000, 20 g, 0.001 moles), di(1-benzotriazolyl)carbonate (3.4 g of 70% mixture, 0.00803 moles), and pyridine (3.0 ml) in acetonitrile (40 ml) was stirred at room temperature under nitrogen overnight. The solvent was removed by distillation and the residue was dissolved in 80 ml of methylene chloride and the resulting solution was added to 800 ml of ethyl ether. The precipitate was collected by filtration and was dried under vacuum at room temperature to yield 16.8 g of product which was shown by $^1$H NMR to be 100% substituted. $^1$H NMR (dmso d-6): 3.23 ppm, CH$_3$O; 3.51 ppm, O—CH$_2$CH$_2$—O; 4.62 ppm, m, mPEG-O—CH$_2$—OCO—; 7.41-8.21, complex mult., benzotriazole protons.

Example 3

Derivatization of Lysine with mPEG$_{20,000}$ BTC

Lysine.HCl (0.0275 g, 0.000151 moles) was dissolved in 26 ml of 0.1 M borate buffer and the pH was adjusted to 8.0 with 0.1 M NaOH. To the resulting solution was added mPEG$_{20,000}$ BTC (7.0 g, 0.00350 moles) over 15 minutes and the pH was kept at 8 by addition of 0.1 M NaOH. After stirring the resulting solution for 3 h, 15 g of H$_2$O and 4 g of NaCl were added and the pH was adjusted to 3.0 with 10% phosphoric acid. The product was extracted with methylene chloride and the extract dried over MgSO$_4$. After concentrating the solution to 30 ml, the solution was poured into 300 ml of ethyl ether and the product collected by filtration and dried under vacuum at room temperature to yield 5.9 g of product as a white solid. Analysis by gel permeation chromatography (Ultrahydrogel 250, column temperature 75° C., aqueous buffer pH 7.2) showed the product to be a mixture of di-N-PEGylated lysine (MW ~40 KDa, 63.05%), mono-N-PEGylated lysine (MW ~20 KDa, 36.95%), and mPEG$_{20,000}$.

Example 4

Derivatization of Lysozyme with mPEG$_{5000}$BTC

To 4 ml of lysozyme solution (3 mg/ml in 50 mM sodium phosphate buffer, pH 7.2) was added 20.3 mg of mPEG$_{5000}$ BTC (5-fold excess of mPEG5000 BTC) and the mixture was continually mixed at room temperature. Analysis by capillary electrophoresis (57 cm×76 um column; 30 mM phosphate buffer; operating voltage 25 kV) after 4 hours showed that 6.94% of unreacted lysozyme remained, while 33.99% of mono-PEGylated lysozyme, 43.11% di-PEGylated lysozyme, 13.03% tri-PEGylated lysozyme, and 2.92% of tetra-PEGylated lysozyme had formed.

Example 5

PEG$_{2KDa}$-α-hydroxy-ω-propionic acid, benzyl ester

To a solution of PEG$_{2KDa}$-α-hydroxy-ω-propionic acid (10 g, 0.0050 moles) (Shearwater Corp.) in anhydrous methylene chloride (100 ml), 1-hydroxybenzotriazole (0.30 g), 4-(dimethylamino)pyridine (1.0 g), benzyl alcohol (10.8 g, 0.100 moles) and 1,3-dicyclohexylcarbodiimide (1.0 M solution in methylene chloride, 7.5 ml, 0.0075 moles) were added. The reaction mixture was stirred overnight at room temperature under argon. The mixture was then concentrated to about 50 ml, filtered and added to 800 ml cold diethyl ether. The precipitated product was filtered off and dried under reduced pressure. Yield 8.2 g. NMR (d6-DMSO): 2.60 ppm (t, —CH$_2$—COO—), 3.51 ppm (s, PEG backbone), 4.57 ppm (t, —OH—), 5.11 ppm (s, —CH$_2$— (benzyl)), 7.36 ppm (m, —C$_6$H$_5$ (benzyl)).

Example 6

PEG$_{2KDa}$-α-benzotriazole carbonate-ω-propionic acid, benzyl ester

To a solution of PEG$_{2KDa}$-α-hydroxy-ω-propionic acid, benzyl ester (8.2 g, 0.0025 moles) in acetonitrile (82 ml), pyridine (0.98 ml) and di(1-benzotriazolyl)carbonate (1.48 g) were added and the reaction mixture was stirred overnight at room temperature under argon atmosphere. The mixture was then filtered and solvent was evaporated to dryness. The crude product was dissolved in methylene chloride and precipitated with isopropyl alcohol. The wet product was dried under reduced pressure. Yield 6.8 g. NMR (d6-DMSO): 2.60 ppm (t, —CH$_2$—COO—), 3.51 ppm (s, PEG backbone), 4.62 ppm (m, —CH$_2$—O(C=O)—), 5.11 ppm (s, —CH$_2$-(benzyl)), 7.36 ppm (m, —C$_6$H$_5$ (benzyl)), 7.60-8.50 ppm (4 m, aromatic protons of benzotriazole).

What is claimed is:

1. A method comprising;
    providing a poly(ethylene glycol)l having one terminal hydroxyl group;
    reacting the terminal hydroxyl group of the poly(ethylene glycol) with di(1-benzotriazolyl)carbonate to form a 1-benzotriazolylcarbonate ester of the poly(ethylene glycol);
    reacting the 1-benzotriazolylcarbonate ester of the poly(ethylene glycol) with lysine to form in one or more steps an amino acid derivative, said amino acid derivative having the following structure:

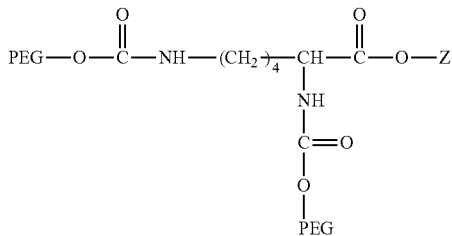

wherein PEG is a poly(ethylene glycol) and Z is selected from the group consisting of H, N-succinimidyl, and 1-benzotriazolyl; and
    reacting the amino acid derivative with a biologically active agent under conditions to form a polymer-active agent conjugate.

2. The method of claim 1, wherein each PEG is capped with a capping group.

3. The method of claim 2, wherein the capping group is methoxy.

4. The method of claim 1, wherein the biologically active agent is a protein.

* * * * *